(12) United States Patent
Babayoff et al.

(10) Patent No.: US 7,255,558 B2
(45) Date of Patent: Aug. 14, 2007

(54) DENTAL IMAGING INSTRUMENT HAVING AIR STREAM AUXILIARY

(75) Inventors: Noam Babayoff, Holon (IL); Eldad Taub, Reut (IL); Avi Kopelman, Ramat Chen (IL)

(73) Assignee: Cadent, Ltd., Or Yehuda (IL)

( * ) Notice: Subject to any disclaimer, the term of this patent is extended or adjusted under 35 U.S.C. 154(b) by 92 days.

(21) Appl. No.: 10/174,271

(22) Filed: Jun. 18, 2002

(65) Prior Publication Data

US 2003/0232302 A1 Dec. 18, 2003

(51) Int. Cl.
*A61C 3/00* (2006.01)

(52) U.S. Cl. ........................................ 433/29

(58) Field of Classification Search .................. 433/29, 433/80, 88, 31, 99; 356/601, 609
See application file for complete search history.

(56) References Cited

U.S. PATENT DOCUMENTS

| 4,184,175 | A |  | 1/1980 | Mullane, Jr. |
| 4,575,805 | A |  | 3/1986 | Moermann et al. |
| 4,725,232 | A | * | 2/1988 | Hatakeyama ................ 433/98 |
| 4,952,149 | A |  | 8/1990 | Duret et al. |
| 5,115,307 | A |  | 5/1992 | Cooper et al. |
| 5,178,536 | A | * | 1/1993 | Werly et al. ................... 433/29 |
| 5,350,299 | A | * | 9/1994 | Gallant ........................ 433/88 |
| 5,381,236 | A |  | 1/1995 | Morgan |
| 5,484,283 | A | * | 1/1996 | Franetzki ..................... 433/116 |
| 5,737,084 | A |  | 4/1998 | Ishihara |
| 6,263,234 | B1 | * | 7/2001 | Engelhardt et al. ......... 600/476 |
| 6,359,680 | B1 |  | 3/2002 | Rubbert |
| 6,386,867 | B1 | * | 5/2002 | Durbin et al. ................ 433/31 |
| 6,468,076 | B2 | * | 10/2002 | Kawamura ................... 433/29 |
| 2002/0055082 | A1 |  | 5/2002 | Durbin et al. |

FOREIGN PATENT DOCUMENTS

WO  WO 00/08415  2/2000

* cited by examiner

*Primary Examiner*—Melba Bumgarner
(74) *Attorney, Agent, or Firm*—The Nath Law Group; Jerald L. Meyer; Derek Richmond

(57) ABSTRACT

A dental instrument and method for imaging the three-dimensional topography of one or more teeth in the oral cavity of an individual is provided. The instrument includes a probe insertable into the oral cavity to receive the image of these surfaces which can then be processed. Combined with the probe is an auxiliary which projects an air stream toward the surface to be imaged by the probe and acts to evaporate and remove from these surfaces a liquid film coating formed by saliva and other fluids present in the oral cavity, to render these surfaces dry and enhance their reflectivity and in doing so, provide clearer images.

16 Claims, 2 Drawing Sheets

DENTAL IMAGING INSTRUMENT HAVING AIR STREAM AUXILIARY

FIELD OF THE INVENTION

This invention relates generally to dental instruments for imaging the three-dimensional topography of teeth in a patient's oral cavity by means of a probe which projects a beam of light toward the surfaces of the teeth and receives reflections therefrom which are processed to derive the required data.

BACKGROUND OF THE INVENTION

It is a standard procedure in dental practice, when necessary to replace defective teeth in the oral cavity of a patient, to first make a cast impression of these teeth. A technician can from these impressions determine the three-dimensional parameters of a denture to replace the teeth.

It is known in order to avoid the need to make cast impressions to directly measure the teeth optically to obtain data for the computer-assisted design (CAD) or computer-assisted manufacture (CAM) of the replacement. In a typical instrument for this purpose, there is provided an optical probe projecting a light beam towards the surfaces of the teeth to be imaged.

The concern of the present invention is with those imaging instruments for direct optical measurement of a set of teeth which includes a probe to be inserted in the oral cavity to project a light beam toward the surfaces of the teeth and to receive light reflected therefrom which is then processed to obtain the digital data for determining the three-dimensional topology of the teeth.

One such instrument for obtaining the three-dimensional parameters of teeth in order to replace the teeth being imaged is disclosed in U.S. Pat. No. 4,575,805. In the patent, the probe takes the form of a scan head which projects a scanning light beam toward the teeth surfaces.

Also disclosing an imaging instrument for the three-dimensional survey of teeth to obtain digital constructional data for the computer-controlled manufacture of a tooth replacement is U.S. Pat. No. 5,381,236. Another such instrument is an intra oral scanner disclosed in U.S. Pat. No. 6,359,680.

Of particular prior art interest is the imaging instrument disclosed in U.S. Pat. No. 6,697,164 filed as Application Ser. No. 09/775,298 on Feb. 1, 2001 (referred to hereinafter as "U.S. Pat. No. 6,697,164") entitled "Imaging A Three-Dimensional Structure by Confocal Focusing an Array of Light Beams". This instrument is provided with a probe in the form of an endoscope which projects light beams toward the surfaces of the teeth to be imaged and receives light reflected therefrom which is processed to obtain the required digital data.

The problem of viewability encountered when using a dental imaging instrument whose probe projects a light beam to illuminate the surfaces of the teeth to be imaged is comparable to that experienced by eyes viewing these surfaces. If the eyes are heavily coated with a tear film, the resultant image will be blurred.

In the case of surfaces of teeth in an oral cavity containing mucous, saliva, and, in some instances, blood resulting from a dental procedure, the surfaces of the teeth are usually then coated with a liquid film composed of these constituents. This liquid film which impairs the ability of an imaging instrument to clearly view the teeth surfaces, cannot easily be dislodged, for tile film is ionically attracted to the teeth surfaces and has a surface tension to protect the integrity of the film and resists its evaporation.

Under ideal circumstances, the surfaces of the teeth to be imaged should be free of liquid and perfectly clean and dry to obtain an optimal degree of reflectivity and image clarity. But this can only happen when the surface reflectivity exhibits a Lambert unit of luminescence. A Lambert unit is defined as the brightness of a perfect diffusing surface that radiates or reflects one lumen per square centimeter A saliva-mucous liquid film coating the teeth surfaces to be illuminated does not act as a perfect diffusing surface and therefore does not exhibit optimal reflectivity. And because this film adheres ionically to the tooth surfaces, it cannot just be washed away.

In common use by dentists is an air suction pipe (negative pressure) to suck out from the oral cavity saliva and mucous which interfere with the dental procedure then in progress. Also in common use is a pressured air pipe (positive pressure) which serves to blow away debris from the region in the oral cavity is working. These pipes must be manipulated by the dentist or his assistant so that the air stream (negative or positive) can be directed to the region of interest.

SUMMARY OF THE INVENTION

In the present invention, an auxiliary producing a positive or negative (suction) air stream is combined with a probe of an imaging instrument which is manipulated in the oral cavity to direct a light beam toward teeth surfaces to be illuminated, the auxiliary then also projecting the air stream in the same direction.

An auxiliary in accordance with the invention is combinable with the light-beam projecting probe of any existing dental imaging instrument adapted to survey the three-dimensional topography of teeth in the oral cavity.

It is thus the main object of this invention to provide a dental image acquisition and method for acquiring an image of the three-dimensional topography of a teeth segment in the oral cavity of a subject by means of a probe projecting a beam of light toward these surfaces, the probe being combined with an auxiliary which causes a stream of gas, typically air, to flow over the surfaces to be illuminated to dry these liquid-film coated surfaces to enhance their reflectivity to give rise to a clearer image of the teeth.

While the invention will be described, by way of example, in conjunction with a dental imagining instrument of the type disclosed in the above-identified U.S. Pat. No. 6,697,164, it is to be understood that it is applicable to any existing form of imaging instrument having a probe which projects a light beam to illuminate the surfaces of the teeth to be imaged.

Among the significant features of the invention, by which a dental imaging instrument is combined with an air stream auxiliary are the following:

A. The auxiliary can project the air stream towards the liquid film coating the surfaces of the teeth to be imaged at a velocity that disrupts the ionic bond between the liquid film and the teeth surfaces.

B. The auxiliary air stream may be made to be in a pulsatory wave form to produce periodic bursts of air which effectively hammer away at the liquid film to dislodge it from the dental surfaces.

C. The air stream may be heated to a temperature level which promotes rapid evaporation of the liquid film coating the teeth surface, which level can be tolerated by the patient.

D. The heated air stream may act to fully dry the teeth surfaces to enhance their reflectivity and in doing so produce clearer images of the teeth.

E. The auxiliary from which the air stream is projected may be integrated with the probe from which a light beam is projected to illuminate the surfaces of the teeth to be imaged whereby the air stream is focused on the surfaces to provide rapid drying thereof.

The invention thus provides, by one of its aspects, a dental instrument for imaging the three-dimensional surface topography of a teeth segment consisting of one or more adjacent teeth in the oral cavity of an individual, e.g. in order to acquire digital data regarding the parameters of a replacement or prosthesis for a missing or broken tooth. The instrument includes a probe insertable into the oral cavity to capture an image of the teeth segment. The probe typically also projects a light beam toward the surfaces of the teeth to be imaged. Alternatively, the illumination may also be an independent light source. The captured image is then conveyed to a processor to obtain the required data. Combined with the probe is an auxiliary which by one embodiment projects an air stream toward the surfaces to be imaged by the probe. The air stream acts to evaporate and remove from these surfaces a liquid film coating formed by saliva and other fluids present in the oral cavity. The surfaces thereby become dry and this enhances their reflectivity, to yield clearer images. By another embodiment, the auxiliary includes a suction arrangement that induces an air stream in an opposite direction that may yield a result comparable to that achieved with the embodiment discussed above. In this matter the film coating is sucked away from the teeth.

By another aspect there is provided a method for imaging the three-dimensional surface topography of a teeth segment. It comprises bringing a probe into proximity of the teeth to be imaged and acquiring the image. The method is characterized in that while acquiring the teeth image causing a stream of gas to flow over the surface of the teeth to be imaged.

In accordance with one embodiment of the invention, said auxiliary induces two air streams, one flowing over the surface of the teeth segment to be imaged, while the other flows over the external optical sensing surface, namely, the external surface of the optical system that acquires the image. In some imaging techniques, e.g. one that makes use of the optical sensing surface such as that disclosed in U.S. Pat. No. 6,697,164 the probe needs to be inserted into the oral cavity and brought into proximity with the teeth to be imaged. In this case, the optical sensing surface may also become coated with a liquid film formed from aerosol particles that exist in the oral cavity or liquid vapor that condenses on the sensing surface.

An optical probe making use of confocal optics is a preferred embodiment in accordance with the invention.

BRIEF DESCRIPTION OF THE DRAWINGS

For a better understanding of the invention as well as other objects and features thereof, reference is made to the annexed drawings in which.

DETAILED DESCRIPTION OF THE INVENTION

As explained above, a dental imaging insolvent of the type disclosed in PCT Publication No. WO 00/08415 or others in which a probe directs a beam of light toward the surfaces of the teeth to be imaged and picks up light reflected from these surfaces, is unable to obtain clear images because the liquid film which coats these surfaces degrade their reflectivity.

A liquid film composed mainly of saliva and mucous present in the oral cavity as well as blood, is ionically adhered to the teeth surfaces and cannot therefore be easily dislodged. The present invention combines the imaging probe with an auxiliary which directs an air stream toward the surface to evaporate the film thereon even though the evaporative process is resisted by the surface tension of the film.

The rate at which liquid is evaporated by a stream of air flowing over its surface depends on the temperature of the air and its velocity. Hence, even when the temperature is fairly high, should the air stream then pass slowly over the liquid surface, the surface tension which acts as a skin covering the liquid will not be disrupted.

The external optical surfaces of the optical sensing probe have to be kept clean of any particles, film, etc., so as to retain good optical qualities required in order to be able to acquire a high quality image. The problem, however, is that the probe needs to be inserted into the oral cavity and consequently such optical surfaces may become coated. particularly by a liquid film, as a result of aerosol particles that exist in the oral cavity or liquid vapor that condenses on such surfaces. Thus, in accordance with one embodiment, the auxiliary provides also a gas stream that flows over such optical surfaces so as to clean such surfaces from any liquid film or droplets that may form thereon.

Figure 1:
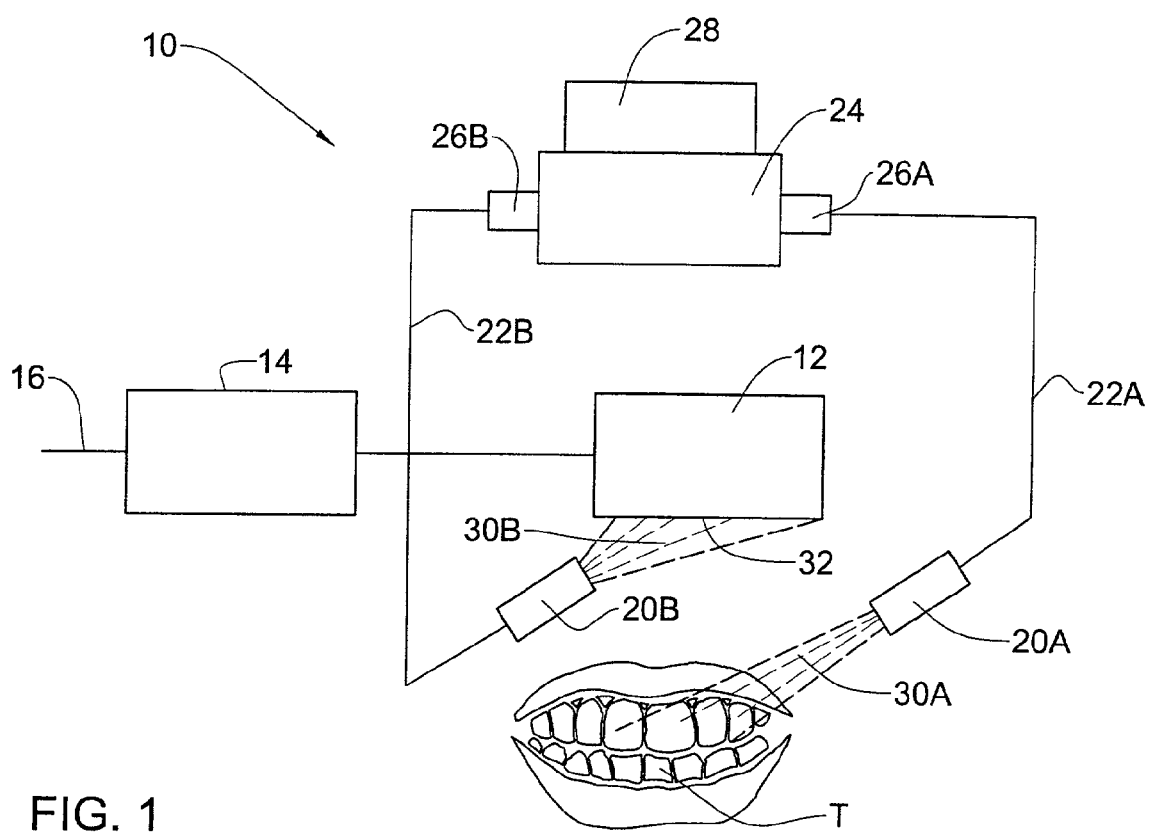
FIG. 1 shows a schematic illustration of an instrument with an auxiliary assembly in accordance with the invention.

Reference is first being made to FIG. 1, showing, in a schematic manner, an optical imaging instrument generally designated 10 that includes an optical probe 12 that can be inserted into the oral cavity and brought into proximity to teeth T and imaging optics and electronics assembly represented by block 14. Block 14 is coupled, through line 16 to an image analysis and data storage computer system (not shown).

The probe and the optical/electronic system may be that disclosed in PCT publication WO 00/008415, the content of which is incorporated herein by reference.

Probe 12 is associated with two nozzles 20A and 20B, each of which is linked through corresponding lines 22A and 22B to a source of pressurized gas 24. Source 24 may be a pressurized gas container or may be a compressor. The source of pressurized gas will typically be located outside the handheld probing instrument (not shown) that houses probe 12 and the optic/electronic assembly 14.

Each of lines 20A and 203 includes also a corresponding flow control valve 26A and 26B. It should be noted that rather than having independent lines, the two lines may combine through a manifold arrangement into a single line that leads to source 24.

In some embodiments of the invention, the gas is beated and a heating source 28 associated with the source of pressurized gas 24 may be provided. In other embodiments, rather than heating the gas at source, the gas may pass through a heat exchanger for online heating before reaching nozzles 20A and 20B. As will be appreciated, the gas is typically air although other gasses such as nitrogen, oxygen and others.

Nozzle 20A is designed to eject a steam of gas 30A towards a segment of the teeth that is to be imaged. The rapid flow of gas, at times heated, over these surfaces, removes the liquid film which otherwise coats the surface of the teeth.

In one preferred embodiment of the invention, a second nozzle 203 is provided which directs the flow of gas towards the optical surface 32 of probe 12. In this way a liquid film or droplets which would otherwise form on surface 32 are removed It should be noted that the instrument may at times be provided with more than one nozzle, such as nozzle 20A or nozzle 20B.

The above description was made in reference to an embodiment where a source of pressurized gas 24 causes a positive flow of gas towards the surface of the teeth T and the surface 32 of probe 12. In other embodiments of the invention, source 24 may be a suction pump giving rise to a negative-pressure air stream, namely from the surface towards the nozzles. A negative air stream will cause air in the oral cavity to flow over the teeth's surfaces, as well as over the optical surface 32 of probe 12 causing the removal of the liquid from such surfaces in this manner. One advantage of negative-pressure air stream is that it will also suck out the vapor evaporated from the liquid film.

Figure 2:
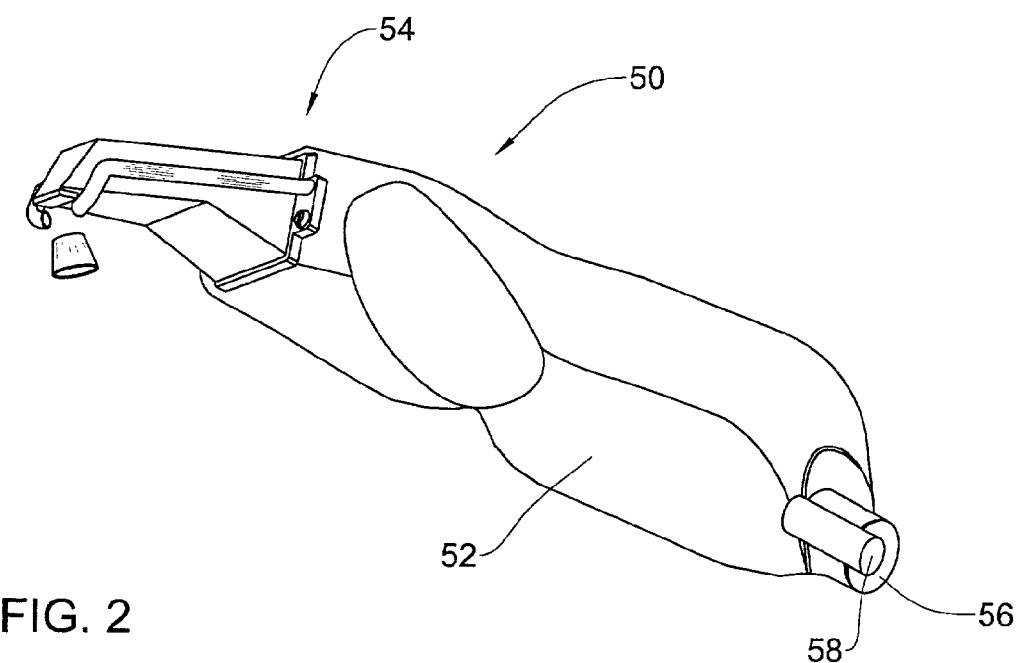
FIG. 2 is a perspective view of a dental imaging instrument incorporating an auxiliary assembly in accordance with the invention.
Figure 3:
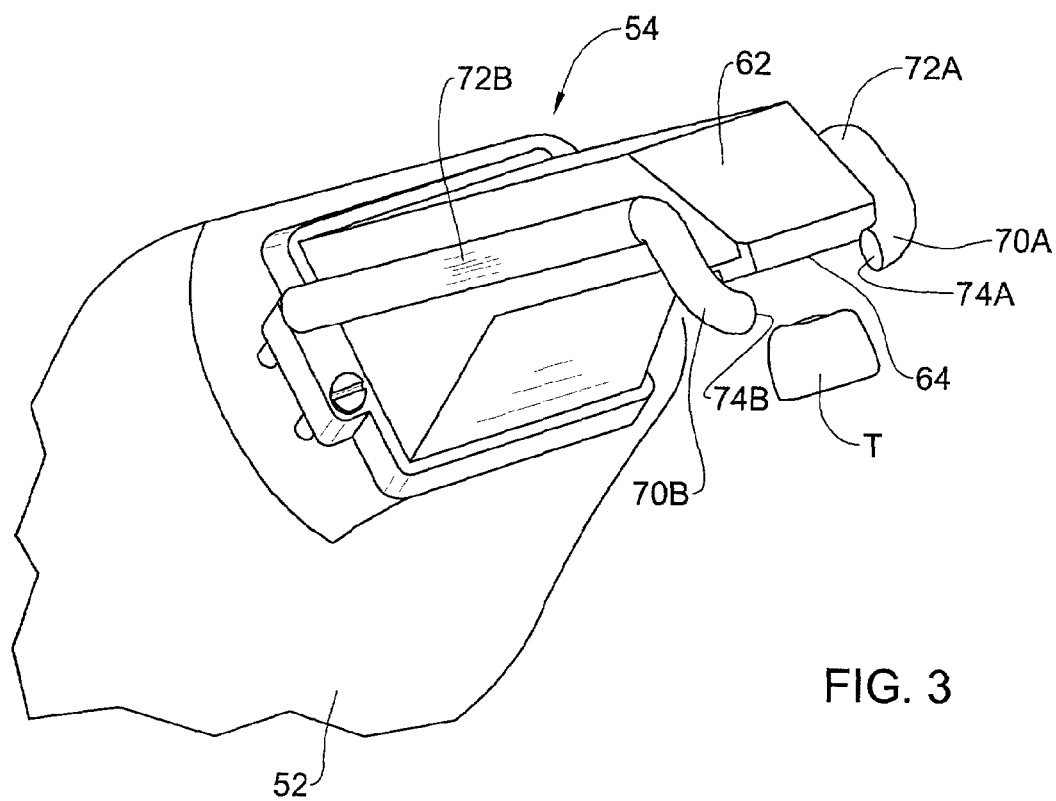
FIGS. 3 and 4 are close-up perspective views, from two different angles, of the front probing portion of the instrument of FIG. 2.
Figure 4:
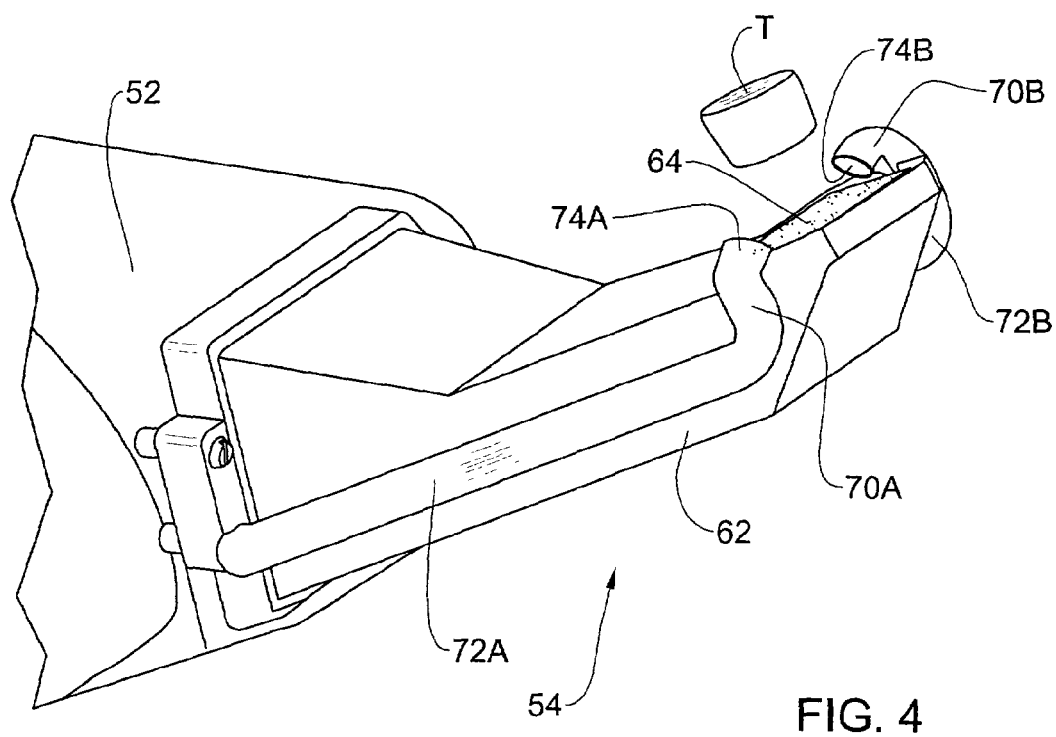

Reference is now being made to FIGS. 2, 3 and 4, showing a handheld probing instrument in accordance with an embodiment of the invention. Instrument 50 has a handle 52 and a head 54. Handle 52 houses the optics electronic assembly that is linked, through connector 56, to an image processing and image storage computers (not shown). Also shown at the rear of handle 52 is a conduit 58 for connecting to a source of pressurized gas (or a vacuum source in accordance with other embodiments of the invention).

The structure of head 54 is best seen in FIGS. 3 and 4. Head portion 54 includes an optical probe 62 designed in the manner shown in FIGS. 2A and 2B of the aforementioned PCT publication WO 00/00815. Optical probe 62 has an external probing glass surface 64 which in use is brought proximal to the teeth to be imaged. For the purpose of illustration, an image of a single tooth T in isolation being proximal and opposite probing glass surface 64, is shown.

Situated on two sides of probe 62 are nozzles 70A and 70B situated at the end of respective straight and rigid tubes 72A and 72B which are linked, through tubings within the handle/housing 52, to gas conduit 58. As can be seen, the opening 74A of nozzle 70A faces the surface to be imaged while opening 74B of nozzle 70B faces glass surface 64. By projecting air out of openings 74A and 74B of nozzles 70A and 70B surface 64 and surface of the tooth will be clean of liquid films or droplets.

In accordance with another embodiment rather than ejecting gas out of these nozzles in a positive ejection fashion, a suction arrangement is provided for sucking air from such surfaces with a similar resulting effect.

The invention claimed is:

1. A dental instrument for determining three dimensional (3D) topography of a teeth segment comprising one or more teeth, said instrument including a handheld probe comprising a probe head having at a distal end thereof an external optical sensing surface adapted for being placed proximal to said teeth segment when in use and through which a beam of light is directed toward said teeth segment and through which light reflected from said teeth segment is received enabling 3D topography to be determined and an auxiliary that directs a stream of gas to said external optical surface of said probe and directs a further stream of gas toward said teeth segment, wherein said auxiliary is directly coupled to said handheld probe.

2. An instrument according to claim 1, wherein said gas of at least one of said stream of gas and said further stream of gas is air.

3. An instrument according to claim 1, wherein at least one of said stream of gas and said further stream of gas is at a temperature above body temperature.

4. An instrument according to claim 1, wherein the determination of 3D topography of a teeth segment is by a suitable imaging means based on the confocal focusing of an array of light beams.

5. An instrument according to claim 1, wherein said probe head is adapted for bringing said optical sensing surface into proximity with respect to a tooth surface such that a distance between said sensing surface and said tooth surface may be generally smaller than a width dimension of the said sensing surface.

6. A dental instrument for determining three dimensional (3D) topography of a teeth segment comprising one or more teeth, said instrument including a handheld probe comprising a probe head having at a distal end thereof an external optical sensing surface adapted for being placed proximal to said teeth segment when in use and through which a beam of light is directed toward said teeth segment and through which light reflected from said teeth segment is received enabling 3D topography to be determined and an auxiliary that directs a stream of gas to said external optical surface of said probe and directs a further stream of gas that is under negative-pressure directed toward said teeth segment, wherein said auxiliary is directly coupled to said handheld probe.

7. A dental instrument for determining the topography of a teeth segment comprising one or more teeth, said instrument including a probe for directing a beam of light toward surfaces of said teeth segment and for picking up light reflected from said surfaces, said probe being suitable for enabling said 3D topography to be determined, an external optical surface on said probe through which said beam of light is directed toward said surfaces of said teeth segment and through which a light reflected from said surfaces is detected and an auxiliary which is directly coupled to said probe and includes a pair of nozzles mounted on laterally opposing sides of the probe, wherein the nozzles are oriented so that one nozzle produces a gas stream with respect to said surfaces of the teeth segment, and the other nozzle produces a gas stream over said external optical surface of the probe.

8. An instrument according to claim 7, wherein the nozzles are coupled to an air compressor.

9. An instrument according to claim 7, wherein the streams of gas are under negative-pressure and the nozzles are coupled to a vacuum pump.

10. An instrument according to claim 7, wherein auxiliary is configured such that at least one of said one nozzle and said other nozzle provides a gas stream in pulsatory wave form.

11. A method for determining a three-dimensional surface topography of a teeth segment comprising one or more teeth, comprising inserting a probe into an oral cavity bringing an external optical sensing surface of the probe into proximity of said teeth segment and directing a beam of light through said external optical surface toward surfaces of said teeth segment and picking up light reflected from said surfaces via said optical surface of said probe, providing streams of gas, wherein one said stream flows with respect to a surface of said teeth segment while picking up said light, and wherein another said stream flows with respect to an said external optical surface of said probe; and processing said picked up light to provide digital data associated with said 3D topography.

12. A method according to claim 11, wherein two said streams of gas can be configured to produce two intersecting sector-shaped gas streams, each sector-shaped gas stream encompassing said teeth to be imaged.

13. A method according to claim 11, wherein at least one of said streams of gas is in pulsatory wave form.

14. A method according to claim 11 wherein said optical sensing surface is brought into proximity with respect to a tooth surface such that a distance between said sensing surface and said tooth surface is generally smaller than a width dimension of the said sensing surface.

15. A method according to claim 11, wherein said optical sensing surface is inserted into the oral cavity when brought into said proximity with the teeth segment.

16. A dental instrument for imaging the topography of a teeth segment comprising one or more teeth to be imaged, said instrument including a probe for capturing an image of surfaces of the teeth segment, an external optical surface on said probe through which a beam of light is directed toward said surfaces of said teeth segment and through which a light reflected from said surfaces is detected, and an auxiliary which directs a stream of gas with respect to these surfaces, wherein said auxiliary is directly coupled to said probe and includes a pair of nozzles mounted on laterally opposed sides of the probe, and wherein the nozzles are oriented so that one nozzle produces a gas stream with respect to said surfaces of said teeth segment, and the other nozzle produces a gas stream over said external optical surface of the probe, and wherein said pair of nozzles are operatively connected to a manifold arrangement adapted for connection to a source.

* * * * *